United States Patent
Higenbottam

[11] Patent Number: 5,839,433
[45] Date of Patent: *Nov. 24, 1998

[54] NITRIC OXIDE TREATMENT

[76] Inventor: Timothy William Higenbottam, Section of Respiratory Medicine, Medical School Floor F, University of Sheffield, Beechhill Road, Sheffield, England, S10 2RX

[ * ] Notice: This patent issued on a continued prosecution application filed under 37 CFR 1.53(d), and is subject to the twenty year patent term provisions of 35 U.S.C. 154(a)(2).

[21] Appl. No.: 624,613

[22] PCT Filed: Oct. 11, 1994

[86] PCT No.: PCT/GB94/02229

§ 371 Date: Jul. 3, 1996

§ 102(e) Date: Jul. 3, 1996

[87] PCT Pub. No.: WO95/10315

PCT Pub. Date: Apr. 20, 1995

[30]    Foreign Application Priority Data

Oct. 12, 1993 [GB] United Kingdom ............... 9320978

[51] Int. Cl.[6] .................................................. A61M 16/00
[52] U.S. Cl. ............... 128/204.21; 128/204.23; 128/283.12; 128/203.25
[58] Field of Search ............... 128/204.21, 204.23, 128/204.18, 200.14, 200.23, 203.12, 203.25, 203.28, 203.29

[56]    References Cited

U.S. PATENT DOCUMENTS

| | | | |
|---|---|---|---|
| 3,612,049 | 10/1971 | Mohson | 128/203.29 |
| 4,681,099 | 7/1987 | Sato et al. | 128/204.23 |
| 4,686,974 | 8/1987 | Sato et al. | 128/204.23 |
| 5,396,882 | 3/1995 | Zapol | 128/200.14 |
| 5,471,977 | 12/1995 | Olsson et al. | 128/204.21 |
| 5,485,827 | 1/1996 | Zapol et al. | 128/200.14 |
| 5,522,381 | 6/1996 | Olsson et al. | 128/203.25 |
| 5,531,218 | 7/1996 | Herbs | 128/203.25 |
| 5,542,415 | 8/1996 | Brody | 128/204.21 |
| 5,570,683 | 11/1996 | Zapol | 128/200.14 |

*Primary Examiner*—John G Weiss
*Assistant Examiner*—V. Srivastava
*Attorney, Agent, or Firm*—Synnestvedt & Lechner

[57]    ABSTRACT

The invention is a method and apparatus for treatment in which nitric oxide is supplied from a source to a patient for inhalation incorporating a regulator to control the flow of nitric oxide from the source to the patient, a monitoring apparatus to monitor the patient's respiration, and a controller to cause the regulator to permit the egress of a very short pulse of nitric oxide of a known, predetermined volume at a predetermined time during the patient's inhalation.

22 Claims, 4 Drawing Sheets

C = CONTINUOUS VENTILATION
VALUES IN BRACKETS = [NO] IN PPM FROM CYLINDER (NO / $NO_2$)
＊$p < 0.05$

NITRIC OXIDE TREATMENT

FIELD OF THE INVENTION

This invention relates to nitric oxide treatment, and concerns in particular the use of nitric oxide in the treatment of certain lung diseases or conditions, and in apparatus for this purpose.

BACKGROUND OF THE INVENTION

There are a number of lung diseases and conditions—suffered both by humans and by other animals, and typified by asthma (an increasingly prevalent and worrying problem)—in which the peripheral parts of the lung, namely those tiny airways and air spaces known respectively as bronchioles and alveoli, constrict to restrict the flow of air therethrough. This can be extremely serious, for it is in these spaces that oxygen in the inhaled air diffuses through the lung tissue into the blood capillaries running therethrough to bind to the haemoglobin in the blood, while carbon dioxide released by the blood diffuses out and is exhaled; obviously, if the movement of air, oxygen and carbon dioxide is significantly reduced by this constriction the situation may become life threatening.

There are additionally a number of lung conditions in which the lung's small peripheral arteries—the pulmonary arteries—also constrict, typically those deep in the lungs where the oxygen tension falls as in an asthmatic attack, pneumonia, or chronic lung diseases like bronchitis and emphysema (and it should also be noted that such constriction often occurs without the causative mechanism being fully explained; this is the so-called primary pulmonary hypertension). Whatever the reason, the result is that the flow of blood to the capillaries is impaired, and the ensuing increase in the resistance to blood flow—the raised pulmonary vascular resistance—may be so severe as to cause the right ventricle of the heart to fail, and death to ensue.

Normally, the flow of blood to the capillaries of the lungs is closely matched by the flow of inhaled air to the alveoli. This allows the oxygen and carbon dioxide to diffuse evenly between blood and air. However, in lung diseases like asthma, pneumonia, bronchitis and emphysema, and where there is acute injury to the lung, such as that following generalised sepsis or the inhalation of smoke and fumes, the flow of air into the alveoli no longer matches with the flow of blood to the capillaries; air goes to parts of the lung no longer receiving blood, while elsewhere the capillaries may be receiving blood but the associated alveoli are not receiving air. It follows that the exchange of oxygen and carbon dioxide is impaired, possibly to the point where death ensues.

The lung tissues concerned are smooth muscle, which operate, to contract or relax, and then to "set" in the state achieved. The actual activator is chemical in nature, and it is usually possible to find, and apply, some other chemical that will either reverse the effect or block the activator's action. Of the several ways in which the constriction of the lung airways can be treated, and the air spaces caused to open up (dilate), effectively all involve the supply to the relevant tissues' smooth muscle of a drug—a chemical—that causes the muscle to relax (and stay relaxed). The most effective treatments for asthma and like conditions involve the inhalation as an aerosol of the chosen chemical in normally inhaled air. However, to deal with the problem of constricted small pulmonary arteries only a few relieving substances are known, and one of the most powerful—that known as prostacyclin, an extremely potent vasodilator—has to be administered on a continuous basis by infusion into a vein and so to the pulmonary arteries.

Another well-known and effective dilating agent for treating both lung problems of the blood-vessel-constriction type and of the asthma airway type is the gas nitric oxide. Nitric oxide (NO) is one of several gaseous oxides of nitrogen commonly found in nature; two others are nitrous oxide ($N_2O$), known as "laughing gas", and at one time used as a general anaesthetic, and nitrogen dioxide ($NO_2$). The latter, to which nitric oxide is converted by a reaction with free oxygen at a rate which is dependent on the nitric oxide concentration, is a highly reactive and rather dangerous gas that dissolves in water to form nitric acid ($HNO_3$) and nitric oxide, and is one of the main constituents of so-called "acid rain".

Nitric oxide is quite normally generated in animal (particularly human) life, starting from available organic nitrogenous materials or even from inorganic nitrogen derivatives (such as nitrates). For example, in the human system there is an enzyme called Nitric Oxide Synthase (NOS) that does this, starting from the amino acid L-arginine, either continuously or upon induction by some other factor (the enzyme thus exists in both "constitutive" and "inducible" isoforms). Nitric oxide is rapidly absorbed by the lung tissue and then into the blood stream, but it is not carried along therein because it reacts very rapidly with the haemoglobin, the oxygen-carrying pigment in red blood cells to form the stable product methaemoglobin (and nitrite and nitrate), by which route the nitric oxide is effectively inactivated.

Much work has been done on the metabolism of nitric oxide in the human body. It is known to enhance nerve conduction, to combine (by nitrosylation) with, and possibly activate, proteins, and to react with certain superoxides to form the rather dangerous, cell-injuring, peroxynitrites. However, its main effect involves a reaction with the enzyme Soluble Guanylate Cyclase (SGC); which is found in the smooth muscle cells of the lung airways and in the pulmonary arteries, as well as in circulatory platelets—the cells in the blood which cause it to clot and form thrombi. In this reaction the nitric oxide activates the SGC (reacting with a haem moiety therein), and as a result there is formed a second messenger compound, cyclic Guanosine MonoPhosphate (cGMP). This cGMP is a relaxer of smooth muscle cells, and so can vasodilate blood vessels, enhancing blood flow therethrough. In the platelet blood cell activation of SGC impedes aggregation, and thus reduces or prevents thrombosis (the undesirable clumping and clotting of blood cells on some unsuitable surface, such as the inside of a blood vessel such as an artery to the heart).

The effects of nitric oxide have already been used, or proposed for use, in the treatment of lung disease and conditions such as asthma, pulmonary hypertension, especially of the neonatal variety, acute lung injury, and even chronic bronchitis and emphysema, where there is a need to dilate the small arteries or airways. It is the achievement of these effects which bears directly on the present invention. More specifically, it is the manner in which nitric oxide is administered, and the apparatus used for this administration, that concerns the invention.

The obvious way to deliver nitric oxide to the sites in the lungs where it is needed is by inhalation. The problem, however, is that the concentration of nitric oxide thus delivered must be high enough to have the required vasodilatory or bronchodilatory effect (at concentrations of 40 ppm, nitric oxide is as effective as prostacyclin, and amounts in the range of from 10 to 120 ppm seem generally satisfactory) and yet low enough to minimize its rapid conversion to the harmful nitrogen dioxide (for which even as much as 5 ppm is considered a dangerous and toxic quantity). As a result, the nitric oxide concentration in the inhaled mixture with air (and sometimes with oxygen-enriched air, with its greater ability to oxidise the nitric oxide to the dangerous nitrogen dioxide) has to be very carefully controlled; this is more difficult than it might seem.

For most lung diseases and conditions to be treated using nitric oxide, the ideal way to administer the required mixture of gases is, with the Patient fully conscious, via a simple face mask, the mask being fed either with the mixture itself or with the two components in controlled quantities. Unfortunately, it is all too easy for the Patient to draw additional air in from around the edges of the mask—they never fit very well—and so dilute the mixture to near or below the effective nitric oxide concentration (and, of course, if the amount of nitric oxide delivered to the mask is high enough to obviate this, then it is high enough also to cause excessive nitrogen dioxide formation). Accordingly, the actually preferred mode of administration to date is via a tube inserted right down into the Patient's lung—the process of insertion is referred to as "intubation", the whole process of intubation and treatment being carried out with the Patient anaesthetized—with the gases, or more suitably an appropriate preformed mixture thereof, being fed in from a mechanical ventilator that pushes the gases in, and then pulls them out again, in effect doing the Patient's breathing for him. Apparatus for doing this is disclosed by Dupuy et al, pp421–428 "Journal of Clinical Investigation", Vol. 90 No: 2, August 1992. Dupuy describes a system that delivers directly into the trachea a fixed concentration of nitric oxide in air at a more or less constant rate matching the normal breathing rate.

In either of these methods, but particularly in the latter, it is extremely desirable to keep a watchful eye on the actual amount of nitric oxide being received deep within the lungs, and to check that the nitrogen dioxide level is below the maximum permitted value. Accordingly, each method is inevitably carried out with the assistance of sampling and analysing equipment to detect the nitric oxide and nitrogen dioxide concentrations and to take some remedial action if appropriate.

SUMMARY OF THE INVENTION

It is clearly desirable to find some better way of administering nitric oxide in the treatment of the sort of lung diseases and conditions to which it is suited, and the invention seeks to put forward such an improved manner, as well as apparatus to carry it out. More specifically, the invention proposes a method of treatment in which the nitric oxide is administered to the Patient not continuously (either in admixture with, or separately but side by side with a supply of, air, oxygen or oxygen-enriched air) but intermittently and in short pulses of known, pre-determined volume at one or more suitable time during each inhalation. In the treatment of the constriction of the small pulmonary arteries the very short pulse of nitric oxide is provided at the start of the inhalation, such that the resultant bolus of nitric oxide mixture inhaled by the Patient has a nitric oxide concentration high enough to have the desired therapeutic effect, even if admixed with some additional air, but is of such short duration (both in time and, as a result, in physical length) that, pushed by the following much larger volume of plain, and therefore nitric oxide-free, air/oxygen, it reaches deeper into the lungs, where it both acts on the small pulmonary arteries and is taken up into the capillaries to react with haemoglobin (so preventing the formation of nitrogen dioxide). By contrast, in the treatment of asthma-like airway diseases or conditions the very short pulse of nitric oxide is timed to fall just before the end of the inhalation. This leaves the nitric oxide in contact with the airway smooth muscle in sufficient concentration to cause relaxation, but because at the end of the inhalation the airway is flushed of all the nitric oxide by the air coming from alveoli and lung periphery, so there is avoided prolonged exposure with the consequent risk of the formation of toxic nitrogen dioxide.

The benefits of this will be clear. Firstly, this manner of administration can be employed on a fully conscious Patient to whom the nitric oxide can be given by way of a simple face mask (although if the Patient has been, or has to be, intubated and mechanically ventilated, then of course the nitric oxide can be delivered to the tube downstream of the ventilator). Secondly, because there is no possibility of the nitric oxide concentration within the lungs ever being higher than the initial concentration in the very short pulse, and because the gas is not present for a sufficient length of time to permit dangerous quantities of nitrogen dioxide to form, there is no need for any invasive and expensive nitric-oxide-concentration sampling equipment.

In operation, the proposed treatment method offers a means of specifically delivering a gaseous nitric oxide mixture to the parts of the lung where it is required and expected to act, and in effect only to those parts. If it is to act on the small pulmonary arteries, then by linking the very short pulse of the nitric oxide mixture to the start of the inhalation the mixture can first allow nitric oxide to diffuse into the smooth muscle of the resistant arteries which are just before the capillaries of the lungs, where nitric oxide will be taken up by the haemoglobin and be inactivated. Little or none of the nitric oxide mixture will stay in the main airways of the lungs, where the uptake of nitric oxide is very slow (and where oxidation to nitrogen dioxide might take place). By placing the nitric oxide mixture at the front of the inhaled breath the remaining gas mixture can have a high oxygen level, and the absolute amount of nitric oxide in the inspirate can be kept at a minimum. Conversely, if the very short pulse of nitric oxide mixture is timed towards the end of the inhalation then it is alright if the nitric oxide is be left in contact just with the airways. Again, high concentrations of oxygen can be used in the preceding breath, the oxygen will be taken up by diffusion in the alveoli, and the exhaled air (with a high concentration of carbon dioxide) will flush the remaining nitric oxide from the lungs. In both cases the therapeutically-optimal concentration of nitric oxide can be used, but with only a small fraction of the breath made up of the nitric oxide mixture so there is a very substantial lessening of the chances of toxic doses being given.

With the benefit of hindsight, and such an explanation, the idea of a pulsed treatment of this sort might seem to be rather obvious. This cannot be so, however, for nitric oxide has been used in the treatment of lung diseases and conditions for several years, despite the well-known problems associated with that use, and yet until now there has been no appreciation of the benefits to be derived from a delivery utilising very short pulses. Indeed, even though equipment for the delivery of pulses of other gases that might be generally required by the body—typically oxygen, as is disclosed in Puritan-Bennett WO 87/06,142 (which describes an oxygen-delivery system employing a demand valve controlled by breath-sensor-driving electronics)—seems to be well known, there has hitherto been no suggestion that there might be some benefit to be derived, enabling treatment of specified parts of the lungs themselves, by delivering nitric oxide in a similar way.

In one aspect, therefore, the invention provides a method of treatment (of the human or animal body) for use in connection with lung disease or conditions of the type that can be treated by the administration of gaseous nitric oxide by inhalation, in which:

the nitric oxide is administered to the Patient, at a concentration high enough to have the desired therapeutic effect, intermittently and in very short pulses of known, pre-determined duration either at the beginning or towards the end of each inhalation, as appropriate to the disease or condition to be treated;

such that in operation the nitric oxide is delivered specifically to the site of interest in the Patient's lung.

In another aspect the invention provides nitric oxide treatment apparatus for carrying out the treatment of a Patient with nitric oxide in connection with a lung disease or condition of the type that can be treated by the administration of gaseous nitric oxide by inhalation, which apparatus comprises:

means for supplying gaseous nitric oxide from a source thereof to the Patient for inhalation thereby, the supply means incorporating regulator means to control the egress of nitric oxide from the source; and means to monitor the Patient's respiration;

which apparatus also includes means to cause the regulator means to permit the egress of a very short pulse of nitric oxide of a known, predetermined duration either at the start or towards the end of an inhalation, whereby the nitric oxide is delivered specifically to the site of interest in the Patient's lung.

The meaning of the term "very short" is discussed in more detail hereinafter.

If the nitric oxide is administered at the beginning of the inhalation, the resultant bolus of inhaled nitric oxide mixture reaches the deeper parts of the lungs to act before being absorbed therein, and before any significant amount of nitrogen dioxide occurs, while if administered toward the end of the inhalation the bolus just reaches the airways only, where it can cause relaxation of any airways constriction before being flushed from the lungs by the exhaled gases.

The invention involves the administration of nitric oxide from a source thereof. Most conveniently, and to facilitate the dispensing of a small, known volume, the nitric oxide is in heavily diluted admixture with an inert carrier, typically nitrogen. A convenient actual source, then, is a cylinder of nitric oxide/nitrogen mixture under pressure, a typical mixture containing as little as 100 ppm nitric oxide in nitrogen down to as low as 10 ppm, conveniently about 40 ppm. As the regulator valve is cracked open so the cylinder pressure drops and some of the mixture expands out of the cylinder, to be delivered to the Patient.

The normal maximum flow rate for the nitric oxide (or, preferably, for the nitrogen-diluted nitric oxide)—that is, the flow rate from the source obtained when the regulator valve is in its normal open position—is chosen to provide a pulse of the required very short duration (as is explained further hereinafter) that nevertheless contains a therapeutically-suitable amount of the nitric oxide. In general, a suitable nitric oxide flow rate can be chosen from a wide range of values, but typically the real nitric oxide flow rate will be around a few millilitres (at NTP, normal temperature and pressure) per minute. Thus, for a nitric oxide source in the form of a 100 ppm nitric oxide/nitrogen mixture the mixture flow rate will be in the units or low tens of litres a minute—say, in the range 5 to 50 l/min, typically 12 l/min.

Of course, because in operation the nitric oxide, already preferably admixed with a carrier such as nitrogen, is—as discussed hereinafter—further conjoined with air, oxygen or oxygen-enriched air immediately prior to its administration to the Patient, the actual overall flow rate of the gas as it is carried into the lungs may be somewhat different from the flow rate of the nitric oxide/nitrogen admixture released from the source. However, the point of the use of a pulse of nitric oxide admixture is that what actually goes into the Patient's airways is a bolus of nitric oxide/nitrogen relatively free of any air/oxygen administered in parallel therewith; it will be understood that what is important is the concentration of the nitric oxide in this bolus, coupled with the physical length thereof (which latter is of course determined primarily by the duration of the very short pulse).

The nitric oxide is administered—that is, it is fed—to the Patient. This administration may take any appropriate form. For example, where the Patient is conscious, and breathing through a mask, the nitric oxide may be delivered along a pipe to the mask, where it is automatically inserted into the air/oxygen also supplied to the mask, the resulting combination being then inhaled by the Patient. Alternatively, where the Patient is unconscious, and is intubated and on a ventilator, then the nitric oxide delivery may again be along a pipe but now into the delivery tube from the ventilator just before it enters the Patient's airways.

In the invention the nitric oxide is taken from a source thereof via regulator means to control the egress of nitric oxide from the source. The regulator is in essence simply a valve that can be opened and shut, conveniently by an electrically-operated solenoid arrangement, to permit a very short pulse, or very small amount, of nitric oxide to leave the source and pass along to the Patient. There are many standard regulators suitable for this type of operation; they need no further comment here.

The nitric oxide is administered to the Patient either together with, or—and preferably—separately but side by side with, a supply of air, oxygen or oxygen-enriched air. This is in itself quite conventional, and needs no further comment here, except perhaps to observe again that the very short pulse method of the invention makes it easier and safer to supply the Patient with high concentrations of oxygen, and still avoid the formation of nitrogen dioxide.

In the invention the nitric oxide is fed to the Patient intermittently and in very short pulses of known, pre-determined volume either at the beginning or towards the end of each inhalation. In this context "intermittently" means, for the most part, once each breath; it is, however, more difficult to give a precise meaning to the term "very short", though for general guidance the following comments may be of assistance. The term "very short" means primarily that the provision of sufficient nitric oxide for each bolus thereof is achieved by supplying the gas for a time period—of the order of a few tens of milliseconds—that is very short compared with the length of an average inhalation (which is about 1.5 second). However, there is more to the shortness of the pulse than just its temporal duration, for, the purpose of the pulse being to provide a bolus of nitric oxide both of relatively high concentration and of relatively short physical length, both the actual flow rate of the nitric oxide (perhaps in its carrier mixture form) as it is fed to the Patient and also the actual concentration of the nitric oxide in that fed gas are important factors. What has been determined by experiment is that for nitric oxide flow rates of the sort discussed hereinbefore—actual nitric oxide rates of a few millilitres (from 1 to 4, say) per minute, or 100 ppm nitric oxide/nitrogen mixture rates of the low tens of litres per minute (typically 12 l/min)—very satisfactory results are obtained using pulse durations of a few tens of milliseconds, and typically 20 to 30 msec. Thus, while it will clearly be understood that what is a "very short" pulse depends upon the flow rate and concentration of the administered nitric oxide, nevertheless it can now be said that the term "very short" means "of the order of a few units or tens of milliseconds". Or, to put it another way, the term means roughly one thousandth of the length of an average inhalation.

The nitric oxide pulse is delivered either at the beginning or towards the end of each inhalation. For the treatment of constriction of the small pulmonary blood vessels the pulse of nitric oxide is timed to occur at the beginning of the inhalation. This pulse is then pushed into the lungs by the subsequent air (or oxygen or air/oxygen). The nitric oxide then penetrates the deeper parts of the lungs, before significant oxidation to nitrogen dioxide, to be absorbed by haemoglobin in the blood. On the other hand, for the treatment of asthma-like diseases the pulse of nitric oxide is timed towards the end of the inhalation, so that for the short time before the following exhalation starts the nitric oxide is only in contact with the airways, and that for only a brief period before it is flushed from the lungs by the exhaled air.

To trigger the nitric oxide pulse (at the beginning or near the end of each inhalation), the invention incorporates means to detect this start (or, alternatively, to detect the end of the immediately-preceding exhalation), and then to cause the regulator means to permit the egress of the desired very short pulse at the appropriate time. Actually detecting the start of an inhalation is comparatively simple, and could be effected by a conventional mechanical pressure-drop responsive arrangement such as the demand valve employed in an aqualung or other underwater breathing apparatus. However, to control not merely the opening of the regulator but also its subsequent closing after a predetermined time requires a little more, and conveniently there is used an electronic system that includes a pressure or other appropriate sensor operatively connected to a small computing device that can be programmed to output to the regulator the appropriate control signals as needed. The sensor can be carried in the Patient's mask, or in the tube into his airways (if his breathing is being mechanically assisted), or in the exhalation port; it can be arranged to detect air flow, using a conventional thermistor arrangement, or—and preferably—to detect directly an actual pressure change (a rise or drop, as appropriate).

Just as the invention will involve the use of any convenient means for supplying the Patient with air, oxygen or oxygen-enriched air to be inhaled mixed with the nitric oxide, so it will as appropriate utilise some suitable face mask, intubation tube, and/or ventilator. None of these need any further comment at this time.

BRIEF DESCRIPTION OF THE DRAWINGS

An embodiment of the invention is now described, though by way of illustration only, with reference both to the Tests described hereinafter and to the accompanying Drawings in which.

DETAILED DESCRIPTION OF THE INVENTION

Figure 1:
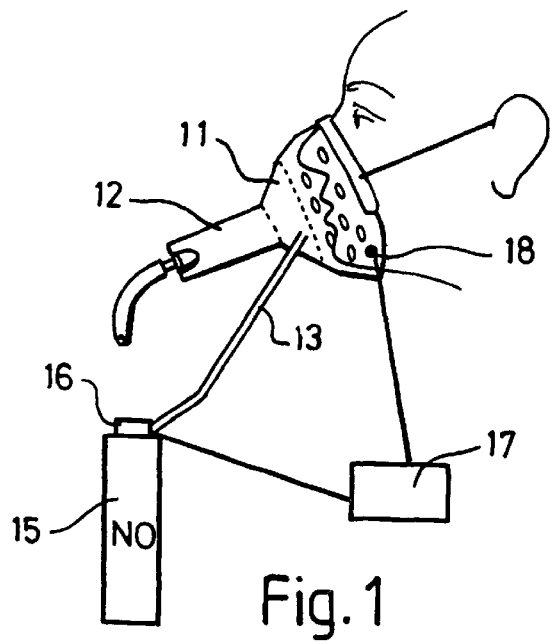
FIG. 1 shows a Patient being treated with nitric oxide according to the invention.

The apparatus shown in use in FIG. 1 is very simple. It comprises a face mask (11) to which an oxygen-enriched air mixture is fed along a first tube (12: from a source not shown) and a nitric oxide/nitrogen mixture ($NO/N_2$) is fed along a second tube (13) from a cylinder (15) thereof. The nitric oxide supply is controlled by a regulator (16) which itself is controlled by a suitably programmed box of electronics (17) driven by signals obtained from a sensor (18) in the mask 11 (the sensor is a thermistor that is cooled by, and so detects, airflow). In this particular case the system is arranged to note the end of an exhalation, and to trigger the operation of the regulator 16 so as to have the pulse of nitric oxide fed into the mask ready for the beginning of the next inhalation.

Figure 2:
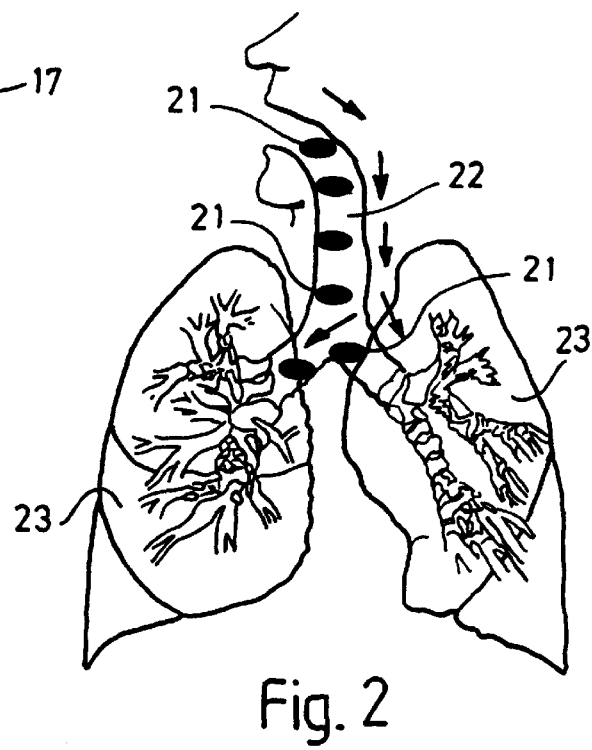
FIG. 2 shows a bolus of nitric oxide/air mixture travelling down deep into the Patient's lungs.

FIG. 2 shows the progress of a bolus (21) of nitric oxide/air mixture down the Patient's windpipe (22) and on deep into his lungs (23). Though at first sight it looks as though there are several bolus preceding one after the other, in fact there is only one, shown at different times on its journey, and the object of the Figure is to show how the bolus remains as an entity, and does not disperse as it progresses (and so reaches the deepest part of the lungs as a concentrated burst of nitric oxide with the full therapeutic effect required).

Figure 3:
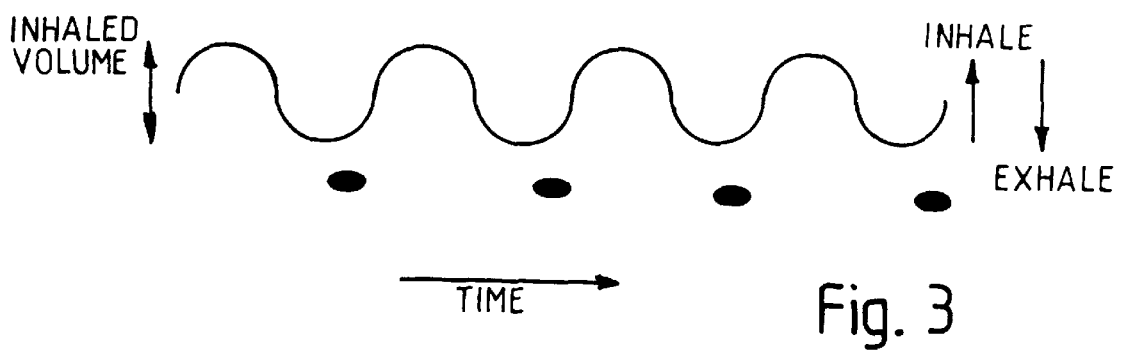
FIG. 3 shows graphically the Patient's respiration, and the timing of the nitric oxide pulses at the start of an inhalation.

The timing of the bolus delivery is shown graphically in FIG. 3. Airflow in and out of the lungs takes place at regular intervals, as the Patient breathes, and just as the flow starts a pulse of nitric oxide is delivered, and "washed down" with the remaining inhaled air.

Figure 4:
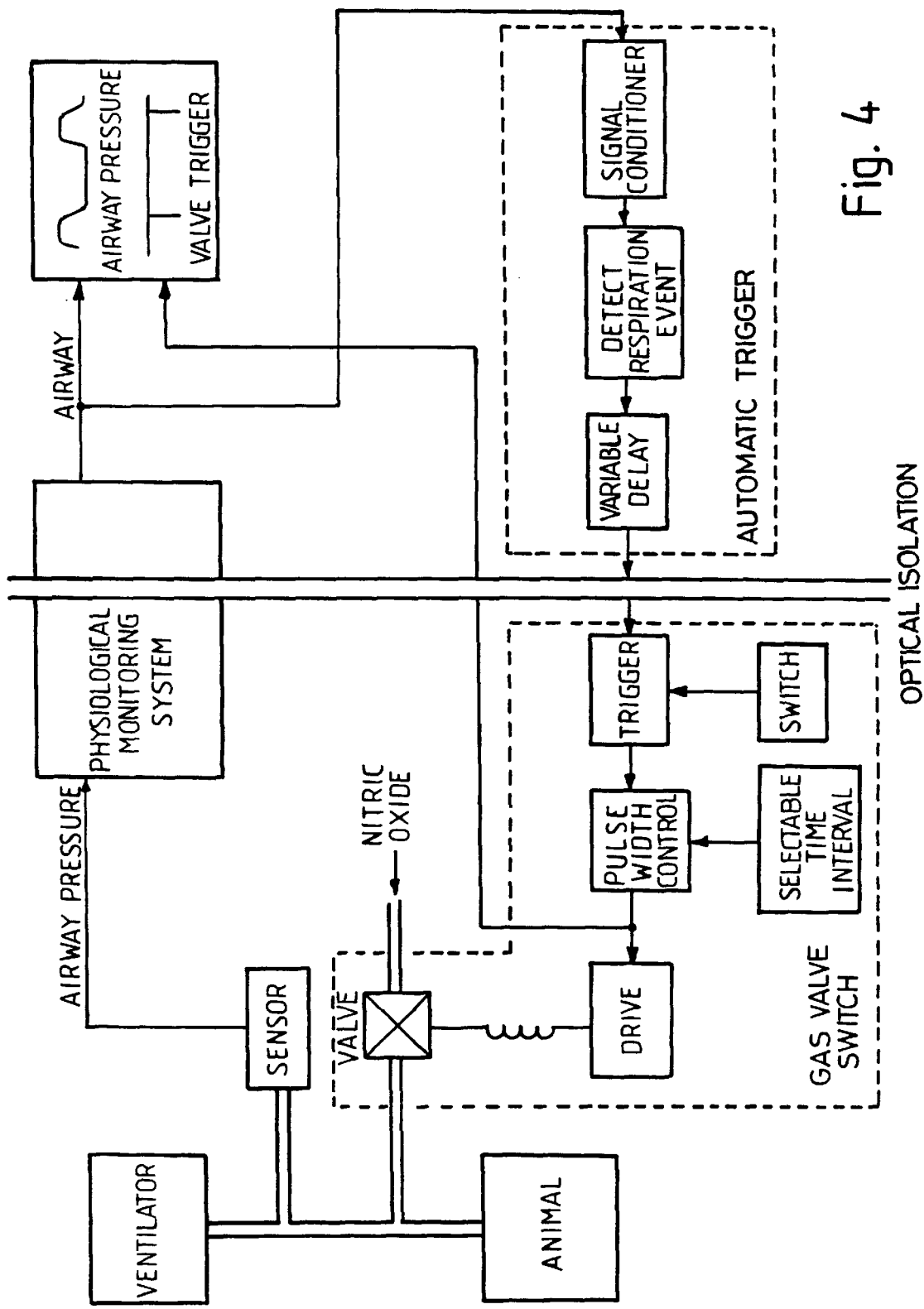
FIG. 4 is a black box schematic of apparatus according to the invention used for providing Test Data relating to the treatment method of the invention.
Figure 5:
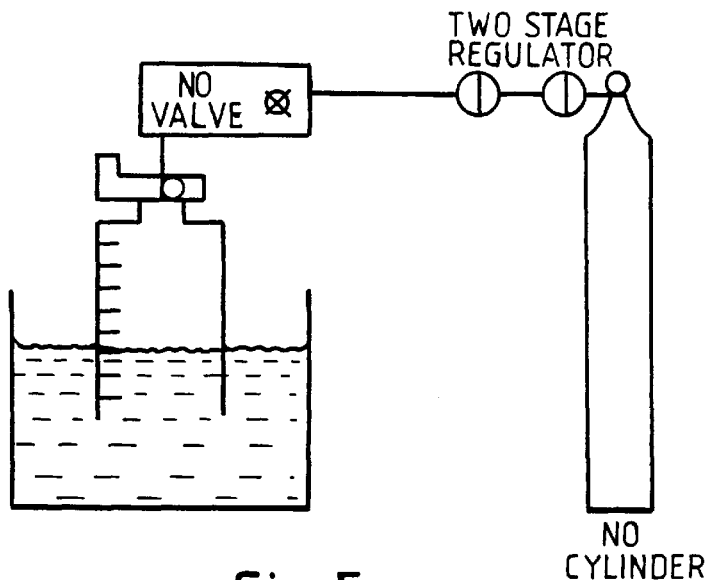
FIG. 5 shows the physical nature of some of the FIG. 4 apparatus.
Figure 6A:
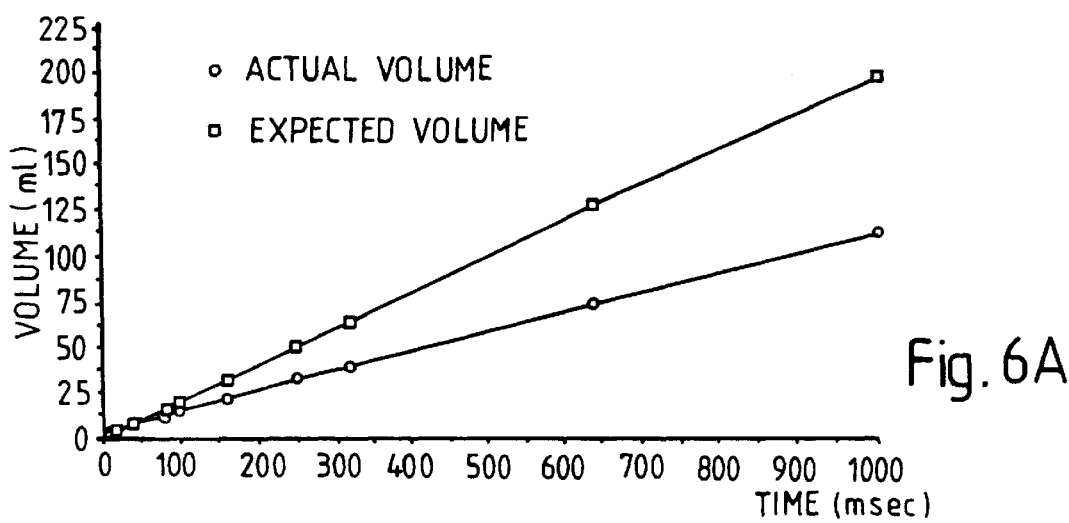
FIGS. 6A/b show graphically values relating to the initial calibration of the FIG. 4 apparatus.
Figure 6B:
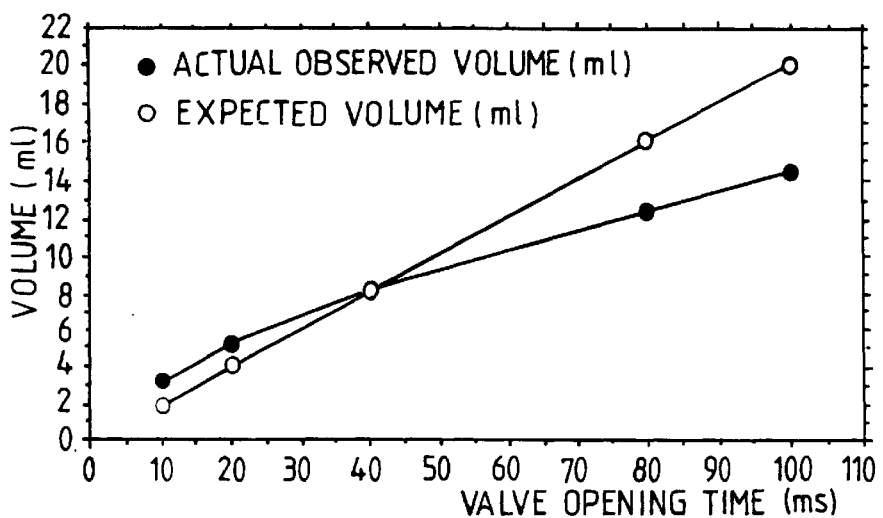

The nitric oxide spike delivery system shown in FIGS. 4 and 5 involves respectively a valve operating system (shown in FIG. 4) and a cylinder containing 100 ppm nitric oxide in a carrier gas diluent such as nitrogen and having a two-stage regulator (FIG. 5). The regulator, which may be of any conventional design, drops the pressure of the 100 ppm nitric oxide/nitrogen mixture so that with a valve-open flow rate of 12 litres per minute opening the valve for 0.5 seconds causes a volume of 100 cc to be delivered. After the main pressure reducing regulator, it is the valve orifice that offers the greatest resistance to flow; therefore it is possible to specify the flow rate from the inlet pressure delivered to this valve. FIG. 5 also shows joined to the valve and cylinder the calibration study equipment; this is used to measure the volume of gas mixture emitted from the valve with various opening times. The results of this study are shown in FIGS. 6A/B, and are discussed below (the actual volumes obtained are there compared with the volumes expected on the basis of the valve having a "square wave" opening form).

Valve operation may be triggered either manually via an external pressure pad switch or automatically. The manual switch acts on the switch shown in FIG. 4, triggering a pulse of predetermined width which then acts on the drive of the valve. The automatic trigger is synchronised to the airway pressure signal shown also in FIG. 4. Once triggered, the period that the valve is open is specified electronically.

A trigger output signal is available from the gas switch unit so that the instant that the nitric oxide spike is delivered during the respiration cycle can be monitored and recorded on the data acquisition system.

Where necessary, signals have been optically isolated to avoid circumvention of the physiological monitoring system electrical isolation barrier.

The actual gas valve switch used in the apparatus has been designed specifically for use in the operating theatre, and accordingly is housed in a fully sealed box (shown by the dashed outline) to prevent the ingress of fluids and permit easy cleaning. The unit operates from a single PP3 style 9 V battery down to a level of 6 V (a low battery indicator is provided).

The valve utilised is a 1.6 mm orifice miniature solenoid valve with stainless steel base block, tube and plunger assembly, and is fitted with an EPDM seal (all of these are as recommended for use with nitric oxide). The coil is operated from a 6 V direct current supply, and has a power rating of 5 watts. Minimum operating time is 10 ms.

In order to maximise battery life, the valve coil is energised at a peak current of 400 mA for 7.5 ms, and then the current is reduced to a holding level of 100 mA for the remaining period that the valve is maintained open. Constant current drive is employed to exploit the full discharge range of the battery. A minimum of one thousand operations with a pulse width of 625 ms should be possible from a high performance Alkaline Manganese (i.e. Duracell PROCELL) battery.

The valve-open time may be set to one of twelve intervals in the range of 10 mS to 2 s. An LED is provided to indicate the state of the valve. The system may be manually triggered from a pneumatic pressure pad switch which permits easy operation either by hand or foot. Alternatively, triggering can be performed automatically, as described below.

In its automatic mode the apparatus includes an automatic trigger that is fed a suitable trigger stimulus derived from the repeated airway pressure output of the physiological pressure monitoring system. The repeated output is an amplified and stabilised version of the sensor signal. However, to ensure reliable detection of a respiratory event (in the Tests described hereinafter, this is the onset of expiration) some further signal conditioning is required. This latter takes the form of a second-order low pass filter (to remove mains interference), zero-offset cancellation, and amplification. The expiration event is then used to initiate a delayed time interval which, once this has elapsed, generates a trigger pulse to the gas valve switch. The delay time is adjustable in the range of 0 to 5 seconds, enabling the automatic trigger to be positioned at any desired point in the respiration cycle. This unit derives its operating power from the +12 V and –12 V rails of the data acquisition system.

In the physiological studies described below the valve assembly was connected to the intratracheal tube use to ventilate the test animal with a Manley Mechanical ventilator. Airway pressure was measured by an air-filled transducer (Spectromed P20, Coventry, UK). The valve was triggered by a fall in the airway pressure on expiration. The switch provided a burst of 100 ppm nitric oxide/nitrogen gas mixture at the start of the inhalation (the start was judged from direct observation of the pressure wave form and an electrical signal from the valve).

By way of contrasting the invention's treatment against that conventionally used in the field, the effects of different times of opening of the switch according to the invention were compared with the situation and results obtaining when the whole of the inhaled volume being made up of nitric oxide in air at a concentration of 40 ppm.

TEST RESULTS

Studies (1) Calibration of the valve

The first study was to determine the volume of gas delivered by the cylinder/valve assembly used in the FIG. 1 apparatus of the invention. This was measured spirometrically; as shown in FIG. 5, a measurement device was constructed to measure the volume displaced from a "floating bell" on a water container. The volume displaced by a series of open times of the valve (from 10 ms to 1 sec) are shown graphically in FIGS. 6A & B (6B shows the 10 to 100 ms range at a larger scale), together with the calculated (expected) volumes delivered by the valve if it operated with total efficiency (i.e. it opened with a "square wave" form). The observed volumes were used to provide the amount of gaseous nitric oxide delivered to the ventilation system in the actual Test experiments discussed further below.

2) The Physiological Studies

Animal Preparation

The experiments providing the desired Test Results were carried out on pigs which weighed between 35 and 60 kg (mean: 45.2 kg).

The animals were obtained from a commercial breeding centre, and were pathogen-free. They were initially sedated with 0.5 mg/kg Droperidol (DROPLEPTAN, from Janssen Pharmaceutical Ltd, Oxon, UK) and 0.3 mg/kg Midazolam (HYPNOVEL, from Roche, Welwyn, UK). A 19–21 gauge intravenous cannula was placed in a peripheral vein of their ear, and sodium pentobarbital (SAGATAL, from Rhone-Polenc, UK) was infused in (at a dose of up to 15 mg/kg) to induce anaesthesia. The infusion was maintained at 9–11 ml/hr up to a maximum of 30 mg/kg. The animal was then intubated through a tracheotomy, and then paralysed with 0.2 mg/kg Alcuronium (ALLOFERIN, from Roche, Welwyn, UK). The ventilator was run at a tidal volume of 500 ml and 15 breaths per minute, and air was used.

The left carotid or femoral artery was cannulated in order to measure systemic arterial pressure. The adequacy of anaesthesia was assessed by monitoring the responses of the heart rate and systemic blood pressure to noxious stimuli.

Access to the thoracic organs was achieved by a midline sternotomy. The pericardium was opened and 1,000 U/kg Heparin (from Paynes & Byrne, Greenford, UK) was administered into the right atrium. Two cannulae (ID 5 mm, from Portex, UK) were placed respectively in the inferior vena cava and in the right ventricle through an incision in the right atrium. The animal was exsanguinated via the cannula in the inferior vena cava while 1–2 l of buffered Krebs-Ringers solution containing 40 gm/l Dextran 70 were concurrently infused into the right ventricle. The rate of infusion was adjusted to keep the systemic arterial blood pressure stable until 3 litres of blood were obtained.

The heart was then stopped by an intracoronary injection of $10^{-3}$ potassium chloride, and a stiff cannula (ID 13 mm) was placed in the main pulmonary artery. Through an incision in the left ventricle, another cannula (ID 16 mm) was retrogradely inserted into the left atrium and secured by heavy silk ties which prevented ballooning of the atrial appendage. The cannulae were then connected to an external perfusion system. Time from cardiac arrest to the start of perfusion was never more than 20 minutes.

The perfusion circuit used a heated jacketed reservoir which received autologous blood from the left atrium. From the reservoir, the perfusate was pumped into the pulmonary artery by means of a roller pump (Watson Marlow Model 5001R, UK). A 150 ml reservoir with a small cushion of air was interposed between the pump and the arterial cannula; this acted as a pulse damper as well as a bubble trap. Perfusate temperature was monitored with a thermistor in the inflow cannula. The height of the venous reservoir could be adjusted to the desired venous pressure. Perfusion was instituted at 10 ml/min/kg, and slowly increased by 10 ml/min/kg steps over an hour until a flow rate of 100 ml/min/kg was reached.

The variables recorded throughout the experiments were cardiac output (pulmonary blood flow) (Q), pulmonary artery pressure (PAP), left atrial pressure (PWP), systemic arterial pressure (SAP), and central venous pressure (CVP). The pulmonary vascular resistance (PVR) was calculated from Q/(PAP-PWP). For the purposes of analysis the analogue outputs of the transducers and ultra-sonic flow metres and, where required, the nitric oxide analyser were sampled on demand by a personal computer (Macintosh SE 30, Apple Computer Inc., Cupertino, Calif., USA) using a 16 bit ADC interface at a sample rate of 500 Hz (MP100, Biopac System, Inc., Goleta, Calif., USA).

Protocols (a) Inhibition of endogenous Nitric Oxide Synthase (NOS) of the Lungs

The inhibition of vascular endothelial NOS was achieved by adding to the perfusion solution the analogue for L-Arginine called $N^G$-nitro-L-arginine methyl ester (L-NAME) (at a rate of 1–2 mg/kg). This causes a rise in both PVR and the systemic vascular resistance (SVR).

(b) Infusion of Thromboxane Analogue

The constrictor was an analogue of Thromboxane called U46619; 10 pmol/min was infused to elevate the PVR some twofold.

(c) Delivery of the Spike of nitric oxide

In the first protocol the nitric oxide/nitrogen cylinder contained 40 ppm. The valve was activated to give in random order (10, 20, 40, 80, 160, 320, 640 and 1000 ms) from the start of the breath. There were four measurements of the PVR over five minutes, and a total of five pigs were studied.

In the second protocol a period of ventilation of the lungs with 40 ppm of nitric oxide in air was compared with the spike. The spike was set at different times of opening of the valve (10, 80, 160 and 320 ms) and the nitric oxide source was a cylinder of 100 ppm of nitric oxide/nitrogen.

Results

Protocol (a)

Figure 7A:
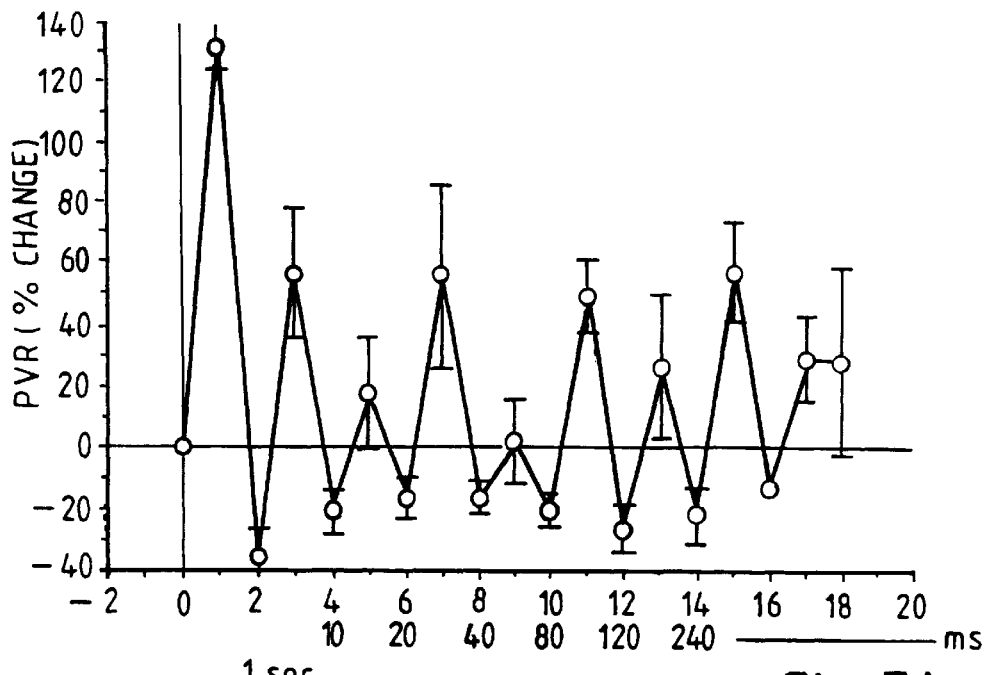
FIGS. 7A/B show graphically some of the results achieved using the FIG. 4 apparatus.

As can be seen from the results shown graphically in FIG. 7A, the pulmonary vascular resistance (PVR) is raised using L-NAME at time 0. Then, with nitric oxide/nitrogen pulses, or spikes, of duration varying from 1 sec down through 240, 120, 80, 40, 20 to 10 msec, it can be seen how the PVR fell to a level below baseline (the zero line). The results show the mean values and the standard deviation. It will be seen that the 10 msec burst of nitric oxide/nitrogen was just as effective as the 1 sec burst.

Protocol (b)

Figure 7B:
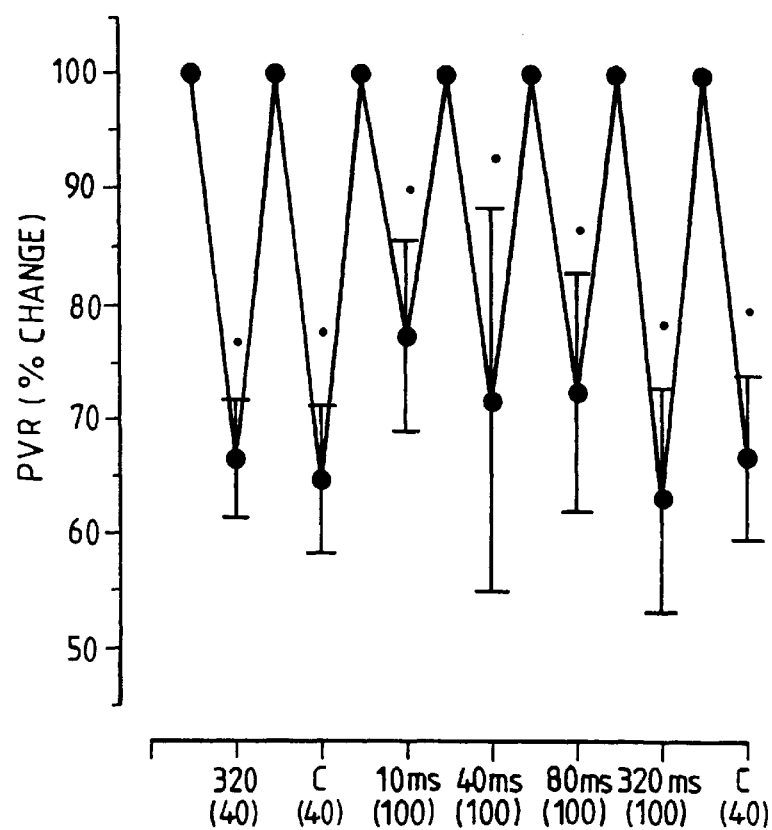

In FIG. 7B the PVR value after administration of U46619 is shown as 100%. The percentage fall in PVR with "spikes" of nitric oxide/nitrogen is compared with continuously-inhaled nitric oxide (shown as C). The control full breath is of nitric oxide at 40 ppm in air whiles the bursts are 100 ppm. Here it can be seen that 10 msec of 10 ppm nitric oxide/nitrogen is as effective as 40 ppm of nitric oxide/air throughout the entire inhalation (ie, as long as one to two seconds).

Conclusion

In the pig lungs where the pulmonary vascular resistance (PVR) is elevated with U46619 and the NOS inhibitor, spiked nitric oxide is as effective as 1 sec or continuous full inhalation of nitric oxide in reducing the PVR. In other words, as little as a 10 ms burst of nitric oxide is equivalent to a whole breath of nitric oxide.

It can be calculated that spiked 0.74 ppm nitric oxide can give the same effect as 40 ppm in the whole breath. Thus, toxicity risk is lessened, there is no need for complex gas mixing, and potentially any breathing pattern can be used.

I claim:

1. An apparatus for carrying out the treatment of a patient with nitric oxide in connection with one of a lung disease or condition of the type that can be treated by the administration of gaseous nitric oxide by inhalation, the apparatus comprising:

means for supplying gaseous nitric oxide from a source thereof to the patient substantially free of any respiratory gas for inhalation thereby, the supply means incorporating regulator means to control the egress of nitric oxide from the source;

means to monitor the patient's respiration; and control means for controlling the regulator to cause the egress from the source of a very short pulse of nitric oxide of a known, predetermined duration at a predetermined instant during an inhalation, the pulse having a duration less than a duration of the inhalation, whereby the nitric oxide is delivered specifically to the site of interest in the patient's lung.

2. An apparatus as claimed in claim 1 which includes the nitric oxide source wherein the nitric oxide is in admixture with an inert gas.

3. An apparatus as set forth in claim 2 wherein the source is a container of nitric oxide/nitrogen mixture under pressure, and contains from 100 ppm to 10 ppm nitric oxide in nitrogen.

4. An apparatus as claimed in claim 1 further comprising:

a face mask; and a pipe coupled between the source and the face mask for providing the nitric oxide to the patient.

5. An apparatus as claimed in claim 1 wherein the nitric oxide is fed to the patient in pulses of from 5 to 50 millisecond duration.

6. An apparatus as claimed in claim 1 wherein the patient's respiration comprises a series of inhalations and exhalations and the control means controls the regulator means to permit the egress of the very short pulse of nitric acid at the start of each inhalation.

7. An apparatus as claimed in claim 6 wherein the means to monitor detects air pressure changes in the patient's respiration.

8. An apparatus as claimed in claim 1 wherein the patient's respiration comprises a series of inhalations and exhalations and the control means controls the regulator means to permit the egress of the very short pulse of nitric acid towards the end of each inhalation.

9. A method for treatment of a patient with nitric oxide in connection with a condition of the type that can be treated by the administration of gaseous nitric oxide by inhalation, the method comprising the steps of:

monitoring the patient's respiration;

administering nitric oxide to the patient at a concentration sufficient to have a desired therapeutic effect intermittently and in very short pulses of known, predetermined duration less than a duration of the patient's respiration and substantially free of any respiratory gas at a specified instant in the patient's respiration as appropriate to treat the condition.

10. A method as set forth in claim 9 wherein the respiration comprises a series of inhalations and exhalations and wherein the instant is at the beginning of each inhalation.

11. A method as set forth in claim 9 wherein the respiration comprises a series of inhalations and exhalations and wherein the instant is towards the end of each inhalation.

12. A method as set forth in claim 9 wherein the nitric oxide is in an admixture with an inert carrier.

13. A method as set forth in claim 12 wherein the nitric oxide is in an admixture with nitrogen in a concentration of 100 ppm to 10 ppm nitric oxide to nitrogen.

14. A method as set forth in claim 13 wherein the very short pulses are 5 to 50 milliseconds in duration.

15. An apparatus for treatment of a patient with nitric oxide comprising:

a source of gaseous nitric oxide;

a regulator coupled to the source to control the flow of the nitric oxide from the source to the patient;

a monitor for monitoring the patient's respiration; and control means responsive to the monitor for controlling the regulator to cause the flow from the source of a very short pulse of nitric oxide of a known, predetermined duration less than a duration of the patient's respiration and at a predetermined instant during the patient's respiration, whereby the nitric oxide is delivered specifically to the site of interest in the patient's lung substantially free of any respiratory gas.

16. An apparatus as set forth in claim 15 wherein the nitric oxide is in admixture with an inert gas.

17. An apparatus as set forth in claim 16 wherein the nitric oxide is in an admixture with nitrogen in a concentration of 100 ppm to 10 ppm nitric oxide to nitrogen.

18. An apparatus as set forth in claim 15 further comprising:

a face mask; and a pipe coupled between the source and the face mask for providing the nitric oxide to the patient.

19. An apparatus as set forth in claim 15 wherein the very short pulse is from 5 to 50 milliseconds in duration.

20. An apparatus as set forth in claim 15 wherein the patient's respiration comprises a series of inhalations and exhalations and the control means controls the regulator means to permit the egress of the very short pulse of nitric acid at the start of an inhalation.

21. An apparatus as claimed in claim 15 wherein the patient's respiration comprises a series of inhalations and exhalations and the control means controls the regulator means to permit the egress of the very short pulse of nitric acid towards the end of each inhalation.

22. An apparatus as claimed in claim 15 wherein the monitor detects air pressure changes in the patient's respiration.

* * * * *